United States Patent
Lee et al.

(10) Patent No.: US 11,484,589 B2
(45) Date of Patent: Nov. 1, 2022

(54) VACCINE COMPOSITION FOR CLASSICAL SWINE FEVER AND PREPARATION METHOD THEREOF

(71) Applicants: BIOAPPLICATIONS INC., Pohang-Si (KR); REPUBLIC OF KOREA (ANIMAL AND PLANT QUARANTINE AGENCY), Gimcheon-Si (KR)

(72) Inventors: Yongjik Lee, Pohang-Si (KR); Dong-Jun An, Anyang-Si (KR); Se Eun Choe, Gwangmyeong-Si (KR); Jae-Young Song, Anyang-Si (KR); In-Soo Cho, Seoul (KR)

(73) Assignees: BIOAPPLICATIONS INC., Pohang-Si (KR); REPUBLIC OF KOREA (ANIMAL AND PLANT QUARANTINE AGENCY), Gimcheon-Si (KR)

( * ) Notice: Subject to any disclaimer, the term of this patent is extended or adjusted under 35 U.S.C. 154(b) by 127 days.

(21) Appl. No.: 16/770,190

(22) PCT Filed: Sep. 16, 2019

(86) PCT No.: PCT/KR2019/011915
§ 371 (c)(1),
(2) Date: Jun. 5, 2020

(87) PCT Pub. No.: WO2020/060117
PCT Pub. Date: Mar. 26, 2020

(65) Prior Publication Data
US 2020/0289641 A1    Sep. 17, 2020

(30) Foreign Application Priority Data

Sep. 19, 2018 (KR) .................... 10-2018-0112445

(51) Int. Cl.
| *A61K 39/225* | (2006.01) |
| *A23K 50/30* | (2016.01) |
| *A61P 31/12* | (2006.01) |
| *C12N 7/00* | (2006.01) |
| *C12N 15/63* | (2006.01) |
| *A61K 39/00* | (2006.01) |

(52) U.S. Cl.
CPC ............ *A61K 39/225* (2013.01); *A23K 50/30* (2016.05); *A61P 31/12* (2018.01); *C12N 7/00* (2013.01); *C12N 15/63* (2013.01); *A61K 2039/542* (2013.01); *A61K 2039/552* (2013.01)

(58) Field of Classification Search
None
See application file for complete search history.

(56) References Cited

FOREIGN PATENT DOCUMENTS

| CN | 106519041 A | 3/2017 |
| KR | 10-2015-0113934 A | 10/2015 |
| KR | 10-2016-0077239 A | 7/2016 |
| KR | 10-1642727 B1 | 7/2016 |
| KR | 10-1732624 B1 | 5/2017 |

OTHER PUBLICATIONS

Madera et al., Toward the development of a one-dose classical swine fever subunit vaccine: antigen titration, immunity onset, and duration of immunity, 2018, J Vet Sci, vol. 19, No. 3, pp. 393-405.*
NCBI, GenBank Accession No. BAM66310.1, 'IgG heavy chain constant region, partial [Sus scrofa]', Nov. 9, 2012.
NCBI, GenBank Accession No. BAM75542.1, 'IgG heavy chain precursor [Sus scrofa]', Jan. 12, 2013.
Extended European Search Report dated Jun. 21, 2022 for the corresponding European Patent Application No. 19862863.8, 11 pages.
Database UniProt [Online] Nov. 12, 2012 (Nov. 12, 2012), "IgG heavy chian constant region, Sus Scrofa (Pig)", XP002806679, Database accession No. UNIPARC:UPI000299C982, 2 pages.

* cited by examiner

*Primary Examiner* — Benjamin P Blumel
(74) *Attorney, Agent, or Firm* — Vorys, Sater, Seymour & Pease LLP; Mih Suhn Koh

(57) ABSTRACT

Provided is a swine fever antigen fused with a porcine Fc fragment, and more particularly, to a vaccine composition having an autoimmune-enhancing effect by binding the Fc fragment to a swine fever antigen, and a preparation method thereof.

14 Claims, 8 Drawing Sheets

Specification includes a Sequence Listing.

| p35S | M17 | BiP | VP1 | pFc | HDEL | NOS |

FIG. 4

FMDV-VP1:pFc1    FMDV-VP1:pFc2    FMDV-VP1:pFc3
  0      1        0      1         0      1

VACCINE COMPOSITION FOR CLASSICAL SWINE FEVER AND PREPARATION METHOD THEREOF

CROSS-REFERENCE TO RELATED APPLICATIONS

This application is a 371 of PCT/KR2019/011915, filed Sep. 16, 2019, which claims the benefit of priority from Korean Patent Application No. 10-2018-0112445, filed Sep. 19, 2018, the contents of each of which are incorporated herein by reference in its entirety.

SEQUENCE LISTING

The Sequence Listing submitted in text format (.txt) filed on Aug. 9, 2022, named "SequenceListing.txt", created on Aug. 9, 2022 (23.2 KB), is incorporated herein by reference.

TECHNICAL FIELD

The present invention relates to an expression vector for producing a classical swine fever antigen E2 protein fused with a porcine Fc fragment, a transgenic organism transformed with the expression vector, a classical swine fever antigen E2 protein fused with a porcine Fc fragment isolated from the transgenic organism, and a use thereof, and the like.

BACKGROUND ART

Classical swine fever is a disease caused by a pathogen, that is, classical swine fever virus (CSFV), and is an infectious disease which infects pigs rather than humans or other animals, but is highly communicable when once contracted by pigs or wild boars, does not have a treatment method, and has a very high lethality with most of the infected pigs dead. Classical swine fever is classified as a very important disease by the World Organization for Animal Health (OIE), is a disease that is classified as one of the Livestock epidemics of category I by the Act on the Prevention of Contagious Animal Diseases even in Korea, and is an infectious disease for which prevention is recognized as an issue important enough to guarantee the future of the pig farming industry without eradication of classical swine fever because the mortality rate and morbidity rate are very high. In Korea, vaccination is performed as a disease countermeasure using a live attenuated vaccine prepared from an LOM strain which is an attenuated live virus, but experts and pig farmers have continuously raised issues regarding the pathogenicity and safety of LOM vaccines (Korean Patent No. 10-1642727).

As representative cases that raise concerns about the safety of LOM vaccine strains, classical swine fever was declared eradicated and a non-vaccination policy was implemented in 2002, but classical swine fever recurred nationwide in 2002 and 2003, so that the LOM vaccination was resumed in all pigs nationwide from 2004, and in this case, many cases of miscarriage and stillbirth occurred after inoculation of pregnant sows, so that there were cases that became issues. Further, on Jeju island, which had been a classical swine fever non-vaccination region since 1999, blood powder preparation products used as additives of feed were distributed while being unintentionally contaminated with a classical swine fever LOM vaccine strain in 2004, and symptoms very similar to classical swine fever occurred in pigs infected with the vaccine strain on 150 farms out of 300 farms on Jeju island, and even during the autopsy of a pig, there have been symptoms of lesions specific to parenchymal organs. Recently, in 2014, it was confirmed that the swine fever LOM vaccine strain was erroneously distributed on Jeju Island and inoculated into pregnant sows, and as a result, miscarriage and stillbirth occurred and the LOM vaccine strain was transmitted vertically to fetuses, so that the issue of vaccine safety is again emerging, and there is a need for an effective vaccine replacing the LOM vaccine strain. Therefore, there is an emerging need for a novel vaccine capable of effectively preventing classical swine fever stably.

DISCLOSURE

Technical Problem

The present invention has been devised in order to solve the problems in the related art as described above, and an object of the present invention is to provide a classical swine fever antigen E2 protein fused with a porcine Fc fragment, a vaccine composition including the same, a preparation method thereof, and the like.

However, the technical problems which the present invention intends to solve are not limited to the technical problems which have been mentioned above, and other technical problems which have not been mentioned will be apparently understood by a person with ordinary skill in the art to which the present invention pertains from the following description.

Technical Solution

The present invention provides a vaccine composition for preventing classical swine fever, including a classical swine fever antigen E2 protein fused with a porcine Fc fragment represented by SEQ ID No. 4 as an active ingredient.

In an embodiment of the present invention, the E2 protein may include an amino acid sequence represented by SEQ ID No. 18, but is not limited thereto as long as the E2 protein is a type of classical swine fever antigen.

In another embodiment of the present invention, the E2 protein is characterized by being fused with the Fc fragment to have an autoimmune-enhancing (self-adjuvanting) effect and increased solubility. The fusion may be in a form in which an antigen is linked to the N-terminus or C-terminus of the Fc fragment by a peptide bond, but is not limited thereto as long as the fusion is in a form in which the Fc fragment and the antigen are bound.

Further, the present invention provides a feed composition for preventing classical swine fever, including a classical swine fever antigen E2 protein fused with a porcine Fc fragment represented by SEQ ID No. 4 as an active ingredient.

In addition, the present invention provides a method for preventing or treating classical swine fever, the method including administering, to an individual, a composition including a classical swine fever antigen E2 protein fused with a porcine Fc fragment represented by SEQ ID No. 4 as an active ingredient.

Furthermore, the present invention provides a use of a composition including a classical swine fever antigen E2 protein fused with a porcine Fc fragment represented by SEQ ID No. 4 as an active ingredient for preventing or treating classical swine fever.

Further, the present invention provides a use of a composition including a classical swine fever antigen E2 protein fused with a porcine Fc fragment represented by SEQ ID No. 4 for producing a medicament used for preventing classical swine fever.

In addition, the present invention provides a recombinant expression vector for producing a classical swine fever antigen E2 protein fused with an Fc fragment, the recombinant expression vector including a polynucleotide encoding a porcine Fc fragment represented by SEQ ID No. 4 and a polynucleotide encoding a classical swine fever antigen E2 protein.

In an embodiment of the present invention, the recombinant expression vector may be sequentially linked so as to be operable in a sequence of a promoter gene, a polynucleotide encoding an E2 antigen, and a polynucleotide encoding an Fc fragment, or so as to be operable in a sequence of a promoter gene, a polynucleotide encoding an Fc fragment, and a polynucleotide encoding an E2 antigen.

In another embodiment of the present invention, the promoter is a cauliflower mosaic virus-derived 35S promoter, a cauliflower mosaic virus-derived 19S RNA promoter, an actin protein promoter of a plant, a ubiquitin protein promoter, a cytomegalovirus (CMV) promoter, a simian virus 40 (SV40) promoter, a respiratory syncytial virus (RSV) promoter, an elongation factor-1 alpha (EF-1α) promoter, a pEMU promoter, an MAS promoter, a histone promoter, a Clp promoter, and the like, but is not limited thereto.

In still another embodiment of the present invention, the recombinant expression vector may further include a polynucleotide encoding a chaperone binding protein (BiP), a gene encoding a His-Asp-Glu-Leu (HDEL) peptide, a 5' untranslated region (5' UTR) site gene of M17, and the like.

In yet another embodiment of the present invention, the recombinant expression vector increases the expression level of a classical swine fever antigen E2 protein fused with an Fc fragment, and the classical swine fever antigen E2 protein fused with the Fc fragment has an autoimmune-enhancing (self-adjuvanting) effect and increased solubility.

Furthermore, the present invention provides a transgenic organism transformed with the recombinant expression vector.

In an embodiment of the present invention, the transgenic organism may be a microorganism such as *Escherichia coli, Bacillus, Salmonella*, and yeast, an insect cell, an animal cell including a human cell, an animal cell such as a mouse, a rat, a dog, a monkey, a pig, a horse, and a cow, *Agrobacterium tumefaciens*, a plant, and the like, the plant may be food crops including rice, wheat, barley, corn, soybean, potato, red bean, oat, and sorghum; vegetable crops including thale-cress, Chinese cabbage, white radish, peppers, strawberry, tomatoes, watermelon, cucumber, cabbage, oriental melon, pumpkins, spring onion, onion, and carrot; specialty crops including ginseng, tobacco, cotton, sesame, sugarcane, sugar beet, perilla, peanut, and rapeseed; fruit including apples, pears, jujubes, peaches, grapes, tangerines, persimmons, plums, apricots, and bananas; flowering plants including roses, carnations, chrysanthemums, lilies, and tulips, and the like, but is not limited thereto as long as it may be an organism which may be transformed with the recombinant expression vector of the present invention.

Further, the present invention provides a method for producing a classical swine fever antigen E2 protein fused with an Fc fragment, which has an autoimmune-enhancing effect, the method including: (a) culturing the transgenic organism; and (b) isolating a classical swine fever E2 protein fused with an Fc fragment from the transgenic organism or culture solution and purifying the classical swine fever E2 protein fused with the Fc fragment. The transgenic organism may be preferably a cell itself, or a culture product including the cell, and the culture solution may be preferably a culture solution from which cells are removed after the cells are cultured, but is not limited thereto as long as it includes a recombinant antigen of the present invention.

Advantageous Effects

Since a classical swine fever antigen E2 protein fused with an Fc fragment according to the present invention has an autoimmune-enhancing effect, even a small amount of the vaccine composition can exhibit an effect of effectively preventing classical swine fever without using an additional immune antigen adjuvant, and the isolation and storage of the antigen is facilitated by increasing the solubility and stability of the antigen. Further, since the production amount of E2 protein can be remarkably increased using the expression vector according to the present invention, it is expected to enable the vaccine to be produced at high efficiency.

DESCRIPTION OF DRAWINGS

FIG. 4 is a view illustrating the result of confirming the stability of a pFc fusion VP1 recombinant protein according to an embodiment of the present invention by western blotting.

MODES OF THE INVENTION

Figures 1, 2:
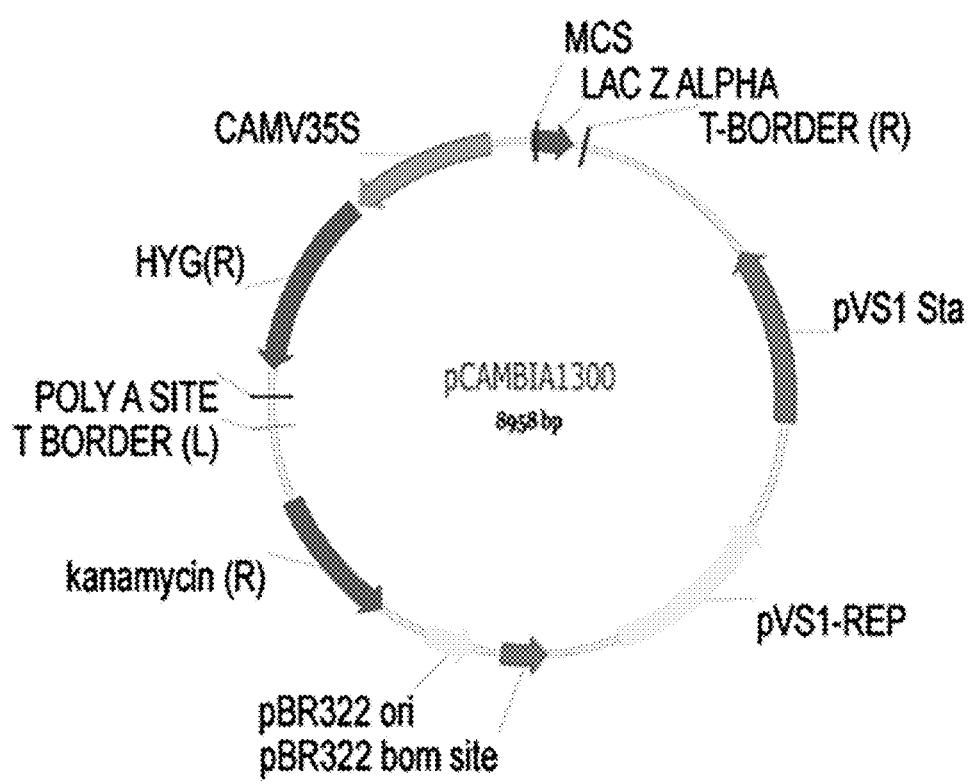
FIG. 1 is a view illustrating a pCAMBIA1300 vector map according to an embodiment of the present invention.
FIG. 2 is a view illustrating the arrangement of genes for expressing a pFc fusion VP1 recombinant protein according to an exemplary embodiment of the present invention.

In the present invention, when a porcine Fc fragment is bound to classical swine antigen E2, it is confirmed that the expression level and productivity of the antigen are increased by the fragment, and solubility and stability are enhanced, and an object thereof is to provide an expression vector including antigen E2 fused with the porcine Fc fragment, a polynucleotide encoding the porcine Fc fragment, and a polynucleotide encoding E2 and a method for producing a recombinant antigen using the expression vector.

As used herein, the "Fc fragment" refers to a portion which is linked only to a heavy chain (H chain) portion by an S—S bond and does not have any antigen binding site when immunoglobulin is digested by papain, and the Fc fragment of the present invention is preferably a porcine Fc fragment, and more preferably a porcine Fc fragment represented by SEQ ID No. 4, but is not limited thereto as long as it is an Fc fragment which increases the expression level and solubility of a target antigen, when fused with the target antigen. Further, the Fc fragment of the present invention includes a variant of SEQ ID No. 4 within the scope of the present invention. Specifically, the gene may include a base sequence having a sequence homology of 90% or more, more preferably 95% or more, and most preferably 98% or more to a base sequence of SEQ ID No. 4. The "% sequence homology" to a polynucleotide is confirmed by comparing a comparison region with an optimally aligned sequence, and a portion of the polynucleotide sequence in the comparison region may further include an addition or deletion (that is, gap) compared to the reference sequence (without addition or deletion) for the optimal alignment of the sequence.

As used herein, the "antigen" generally refers to all materials that cause an immune response in the body, and is preferably a virus, a chemical, a bacterium, pollen, a cancer cell, shrimp, and the like or a partial peptide or protein thereof, but is not limited thereto as long as it is a material that may cause an immune response in the body.

In the present specification, the "classical swine fever virus" belonging to the Pestivirus has an antigen binding site in the E2 glycoprotein which is one type of an approximately 12.3 to 12.5 kb-sized envelope-associated glycoprotein (E protein), so that the E2 protein of classical swine fever virus is known to induce a virus neutralizing antibody response and play an immunologically important role in the defense mechanism of classical swine fever. The E2 protein of classical swine fever virus is also referred to as gp55, and is preferably represented by an amino acid sequence of SEQ ID No. 18. Further, the E2 protein of the present invention includes a variant of SEQ ID No. 17 within the scope of the present invention. Specifically, the gene may include a base sequence having a sequence homology of 70% or more, more preferably 80% or more, and most preferably 90% or more to a base sequence of SEQ ID No. 17.

As used herein, "vaccine" is a biological preparation containing an antigen that causes an immune response in an organism, and refers to an immunogen that induces immunity in an organism by injection or oral administration into a human or animal for prevention of an infectious disease. The animal is a human or non-human animal, and the non-human animal refers to a pig, a cow, a horse, a dog, a goat, a sheep, and the like, but is not limited thereto.

In the present specification, the "target protein" refers to a protein to be produced by a genetic engineering method according to the present invention, and is preferably an antigen that is used commercially and needs to be produced in large amounts, and more preferably an antigen, an antibody, a fragment of an antibody, a structural protein, a regulatory protein, a transcription factor, a toxin protein, a hormone, a hormone analogue, a cytokine, a yeast, a fragment of a yeast, an enzyme inhibitor, a transport protein, a receptor, a fragment of a receptor, a biological defense inducer, a storage protein, a movement protein, an exploitive protein, a reporter protein, and the like, but is not limited thereto as long as the target protein is a protein that can be produced by a recombinant expression vector of the present invention.

As used herein, the "recombinant vector" refers to a vector capable of expressing a peptide or protein encoded by a foreign nucleic acid inserted in the vector, preferably a vector prepared so as to express a target antigen to which a porcine Fc fragment is fused. The "vector" refers to any mediator for the introduction and/or transfer of a base in a host cell in vitro, ex vivo, or in vivo, and may be a replicon to which another DNA fragment may be bound to bring about the replication of the bound fragment, and the "replicon" refers to any genetic unit (for example, a plasmid, a phage, a cosmid, a chromosome, a virus, and the like) that functions as an autonomous unit of DNA replication in vivo, that is, one which is capable of replication under its own control. The recombinant expression vector of the present invention may include preferably a promoter that is a transcription initiation factor to which RNA polymerase binds, any operator sequence for regulating transcription, a sequence encoding a suitable mRNA ribosome binding site, a sequence regulating termination of transcription and translation, a terminator, and the like, more preferably may further include a 5' UTR site gene of M17 for increasing the synthesis amount of a protein, a BiP gene for transferring a target protein to the endoplasmic reticulum, an HDEL gene for minimizing the degradation of a protein such that the protein may be stably maintained in the endoplasmic reticulum, and the like, and even more preferably may further include a tag gene for easily isolating a recombinant protein and a selection marker gene such as an antibiotic resistance gene for selecting a transgenic organism, and the like.

The tag gene is further included for easy isolation in addition to an Fc fragment which is the tagged protein of the present invention, representative examples thereof may include an Avi tag, a Calmodulin tag, a polyglutamate tag, an E tag, a FLAG tag, a HA tag, a His tag, a Myc tag, an S tag, a SBP tag, an IgG-Fc tag, a CTB tag, a Softag 1 tag, a Softag 3 tag, a Strep tag, a TC tag, a V5 tag, a VSV tag, an Xpress tag, and the like, representative examples of the selection marker gene include herbicide resistance genes such as glyphosate or phosphinothricin, antibiotic resistance genes such as kanamycin, G418, Bleomycin, hygromycin, and chloramphenicol, aadA genes, and the like, representative examples of the promoter include a pEMU promoter, a MAS promoter, a histone promoter, a Clp promoter, a cauliflower-mosaic-virus-derived 35S promoter, a cauliflower-mosaic-virus-derived 19S RNA promoter, an actin protein promoter of plant, a ubiquitin protein promoter, a cytomegalovirus (CMV) promoter, a simian virus 40 (SV40) promoter, a respiratory syncytial virus (RSV) promoter, an elongation factor-1 alpha (EF-1a) promoter, and the like, representative examples of the terminator include a nopaline synthase (NOS), a rice amylase RAmy1 A terminator, a phaseolin terminator, a terminator of an octopine gene of *Agrobacterium tumefaciens*, a rrnB1/B2 terminator of *E. coli*, and the like, but the examples are illustrative only and are not limited thereto.

As used herein, the "fusion antigen" refers to a recombinant antigen obtained by fusing a porcine Fc fragment with a target antigen, and preferably refers to a recombinant antigen that preferably has simultaneously increased solubility and immunogenicity by being fused with the Fc fragment, but is not limited thereto as long as it is a recombinant antigen bound to the porcine Fc fragment of the present invention.

As used herein, the "transformation" collectively refers to those processes in which genetic properties of a living organism are changed by injected DNA, the "transgenic organism" is an organism prepared by injecting an external gene by a molecular genetic method, preferably an organism transformed by a recombinant expression vector of the present invention, and the organism is not limited as long as it is a living organism such as a microorganism, a eukaryotic cell, an insect, an animal, and a plant, and is preferably *Escherichia coli, Salmonella, Bacillus*, yeast, an animal cell, a mouse, a rat, a dog, a monkey, a pig, a horse, a cow, *Agrobacterium tumefaciens*, a plant, and the like, but is not limited thereto. The transgenic organism may be prepared by a method such as transformation, transfection, *Agrobacterium*-mediated transformation, particle gun bombardment, sonication, electroporation, and polyethylene glycol (PEG)-mediated transformation, but is not limited as long as it is a method capable of injecting the vector of the present invention.

As used herein, the "solubility" refers to the degree to which a target protein or peptide can be dissolved in a solvent suitable for being administered to a human body. Specifically, the solubility may indicate the degree to which a solute is saturated in a given solvent at a specific temperature. The solubility may be measured by determining the saturated concentration of the solute, and for example, an excessive amount of solute is added to a solvent, the resulting mixture is stirred and filtered, and then the concentration may be measured using a UV spectrophotometer, HPLC, or the like, but the method for measuring the solubility is not limited, and high solubility is advantageous in the isolation and purification of a recombinant protein, and has an advantage in that aggregation of the recombinant protein is inhibited, and thus physiological activity or pharmacological activity of the recombinant protein is maintained.

As used herein, the "prevention" refers to all actions that suppress classical swine fever or delay the onset of the classical swine fever by administering the vaccine composition according to the present invention.

As used herein, the "treatment" refers to all actions that suppresses classical swine fever, alleviate the severity of the disease, or cure or treat the disease by administering a recombinant protein in which the porcine Fc fragment according to the present invention is fused with a target antigen.

As used herein, the "individual" refers to a subject to which the vaccine composition of the present invention may be administered, and the subject is not limited.

The "vaccine composition" of the present invention may be used by being formulated in the form of an oral administration such as a powder, a granule, a tablet, a capsule, a suspension, an emulsion, a syrup, and an aerosol, and a sterile injection solution, according to a typical method. When the composition is prepared, the composition may be prepared using a commonly used diluent or excipient, such as a filler, an extender, a binder, a wetting agent, a disintegrant, and a surfactant. A solid formulation for oral formulation includes a tablet, a pill, a powder, a granule, a capsule and the like, and the solid formulation may be prepared by mixing at least one excipient, for example, starch, calcium carbonate, sucrose or lactose, gelatin, and the like with a lecithin-like emulsifier. Further, in addition to simple excipients, lubricants such as magnesium stearate and talc may also be used. As a liquid formulation for oral administration, a suspension, a liquid for internal use, an emulsion, a syrup, and the like may be used, and in addition to water and liquid paraffin which are simple commonly used diluents, various excipients, for example, a wetting agent, a sweetener, an aromatic, a preservative, and the like may be included. Examples of a formulation for parenteral administration include an aqueous sterile solution, a non-aqueous solvent, a suspension, an emulsion, and a freeze-dried preparation. As the non-aqueous solvent and the suspension, it is possible to use propylene glycol, polyethylene glycol, a vegetable oil such as olive oil, an injectable ester such as ethyl oleate, and the like. Furthermore, an "immune antigen adjuvant" conventionally known may be further included. The adjuvant may be used without limitation as long as it is known in the art, but for example, immunogenicity may be enhanced by further including Freund's Complete Adjuvant or Incomplete Adjuvant.

The vaccine composition or pharmaceutical composition of the present invention may be used by being formulated in the form of an oral formulation such as a powder, a granule, a tablet, a capsule, a suspension, an emulsion, a syrup, and an aerosol, and an external preparation, a suppository, or a sterile injection solution, according to a typical method.

The route of administration of the vaccine composition according to the present invention includes, but is not limited to, oral, intravenous, intramuscular, intraarterial, intramedullary, intrathecal, intracardiac, transdermal, subcutaneous, intraperitoneal, intranasal, intestinal canal, topical, sublingual or rectal routes. Oral or parenteral administration is preferred. As used herein, the term "parenteral" includes subcutaneous, intradermal, intravenous, intramuscular, intraarticular, intrasynovial, intrasternal, intrathecal, intralesional and intracranial injection or infusion techniques. The vaccine composition of the present invention may also be administered in the form of a suppository for rectal administration.

The dose of the vaccine composition or pharmaceutical composition according to the present invention is selected in consideration of the age, body weight, sex, physical condition and the like of the individual. The amount required to induce an immunoprotective response in an individual without particular side effects may vary depending on the recombinant protein used as an immunogen and any presence of an excipient. In general, each dose contains 0.1 to 1000 μg, preferably 0.1 to 100 μg of a protein per ml of a sterile solution of the recombinant protein of the present invention. In the case of the vaccine composition, an initial dose followed by optionally repeated antigenic stimulation may be performed, if necessary.

As used herein, the "immune antigen adjuvant" generally refers to any material that increases a humoral and/or cellular immune response to an antigen, and the "self-immune enhancing response" (self-adjuvanting) refers to a response in which the recombinant antigen itself increases the humoral and/or cellular immune response to the antigen as compared to an existing antigen, and preferably means that the immunogenicity of the antigen is increased by binding a porcine Fc fragment to an antigen.

The "feed composition" of the present invention refers to feed including a classical swine fever antigen E2 protein fused with the Fc fragment of the present invention, examples of the feed include byproducts such as pork, beef, and chicken, and corn, rice, general rice straw, wild grass, grass, silage, hay, mountain wild grass, and the like, but are not limited thereto, and may be used without limitation as long as it is used for raising livestock. Examples of a method for adding the E2 protein of the present invention to the feed and blending the resulting mixture include a method such as mechanical mixing, adsorption, and occlusion, but are not limited thereto.

Hereinafter, preferred examples for helping the understanding of the present invention will be suggested. However, the following examples are provided only to more easily understand the present invention, and the contents of the present invention are not limited by the following examples.

EXAMPLES

Example 1: Preparation of pFc Fusion VP1 Recombinant Protein Expression Vector

In order to prepare an expression vector for producing a recombinant protein with enhanced isolation and purification efficiency by increasing the expression level of a target protein and simultaneously improving solubility, an expression vector was constructed using pFc1 (SEQ ID No. 1), pFc2 (SEQ ID No. 3), or pFc3 (SEQ ID No. 5) of a porcine Fc fragment (pFc). More specifically, as illustrated in FIGS. 1 and 2, an expression vector was constructed by cloning a 5' untranslated region (UTR) site gene (SEQ ID No. 7) of M17, a polynucleotide (SEQ ID No. 8) encoding a chaperone binding protein (BiP) protein, a VP1 gene (SEQ ID No. 9) of Foot-and-mouth disease virus (FMDV), a polynucleotide encoding a pFc fragment, and a polynucleotide encoding a His-Asp-Glu-Leu (HDEL) protein in this order between a CaMV 35S promoter gene and a NOS terminator of a pCAMBIA1300 vector. Different expression vectors were constructed by inserting each of pFc1, pFc2, or pFc3 as the pFc fragment.

Example 2: pFc Fusion VP1 Recombinant Protein Expression Experiment 2.1. Experiment for Confirming Expression Level of pFc Fusion VP1 Recombinant Protein In order to confirm the protein expression level of the pFc fusion VP1 recombinant protein expression vector constructed in the same manner as in Example 1, a transgenic organism was prepared by introducing the vector into a protoplast isolated from thale-cress leaves by a PEG-mediated transformation method, and then the expression pattern of BiP:FMDV-VP1:pFc, which is a recombinant protein expressed therefrom by collecting and dissolving the cultured protoplast was confirmed by western blotting using an anti-pig secondary antibody (1:5,000, Abcam) recognizing pFc. More specifically, 30 µL of cell lysate was mixed with an SDS sample buffer, and then heated. Next, proteins were isolated by size by subjecting 10% SDS-PAGE gel to electrophoresis, an isolated protein was transferred to a PVDF membrane, and then subjected to a blocking step using 5% skim milk, and then an antigen and the protein were bound to each other, and treated with an ECL solution by the method provided by the manufacturer, thereby confirming a pFc fusion recombinant protein. The results are illustrated in FIG. 3.

Figure 3:
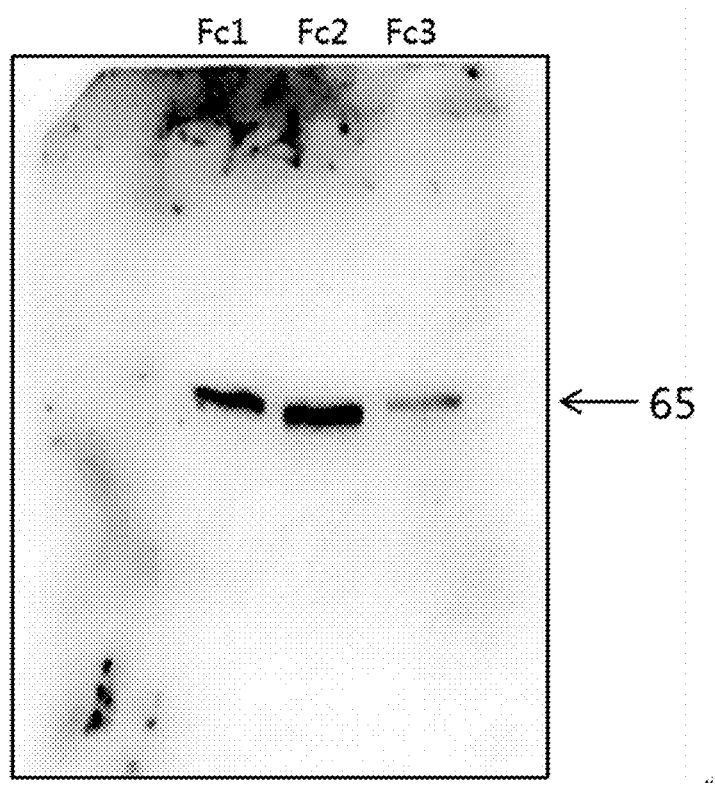
FIG. 3 is a view illustrating the result of confirming the expression level of a pFc fusion VP1 recombinant protein according to an embodiment of the present invention by western blotting.

As illustrated in FIG. 3, it was confirmed that among various pFc fragments, the recombinant protein to which the pFc2 fragment was bound had the highest expression level. Through the result, it could be confirmed that the same immunoglobulin fragments did not show the same effect.

2.2. Experiment for Confirming Stability of pFc Fusion VP1 Recombinant Protein

In order to confirm the protein stability of the pFc fusion recombinant protein expression vector prepared in the same manner as in Example 1, the protein stability was confirmed by respectively performing western blotting in the same manner as in Example 2.1 on the sample (0) when the recombinant protein was extracted and the sample (1) after the sample (0) was stored at 4° C. for 1 hour. The results are illustrated in FIG. 4.

Figure 4:
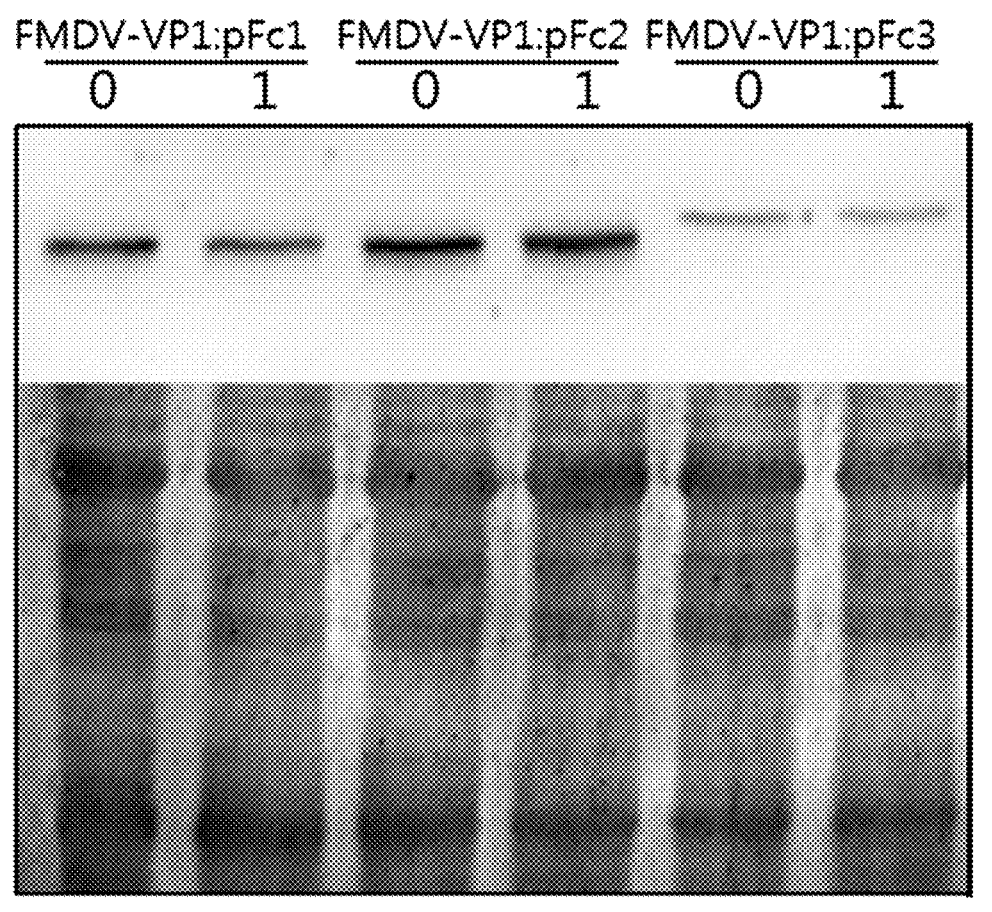

As illustrated in FIG. 4, it was confirmed that the expression level of the recombinant protein to which the pFc2 fragment was bound was highest, and stability was also high.

2.3. Experiment for Confirming Solubility of pFc2 Fusion VP1 Recombinant Protein In order to confirm the protein solubility of the pFc2 fusion recombinant protein expression vector prepared in the same manner as in Example 1, after a pFc2 fusion recombinant protein (BiP:FMDV-VP1:pFc2) was expressed by a transient expression method for inoculating *Agrobacterium tumefaciens* transformed with the vector into leaves of a tobacco plant (*Nicotiana benthamiana*), a protein was extracted from the plant leaves and centrifuged, and then western blotting was performed in the same manner as in Example 2.1 using a protein in a soluble form (S) included in the solution and a protein present in the pellet (P) part. As a control, a recombinant protein fused with a polynucleotide (SEQ ID No. 13) encoding a conventionally known cellulose binding module (CBM3) instead of the pFc fragment was used. The results are illustrated in FIG. 5.

Figure 5:
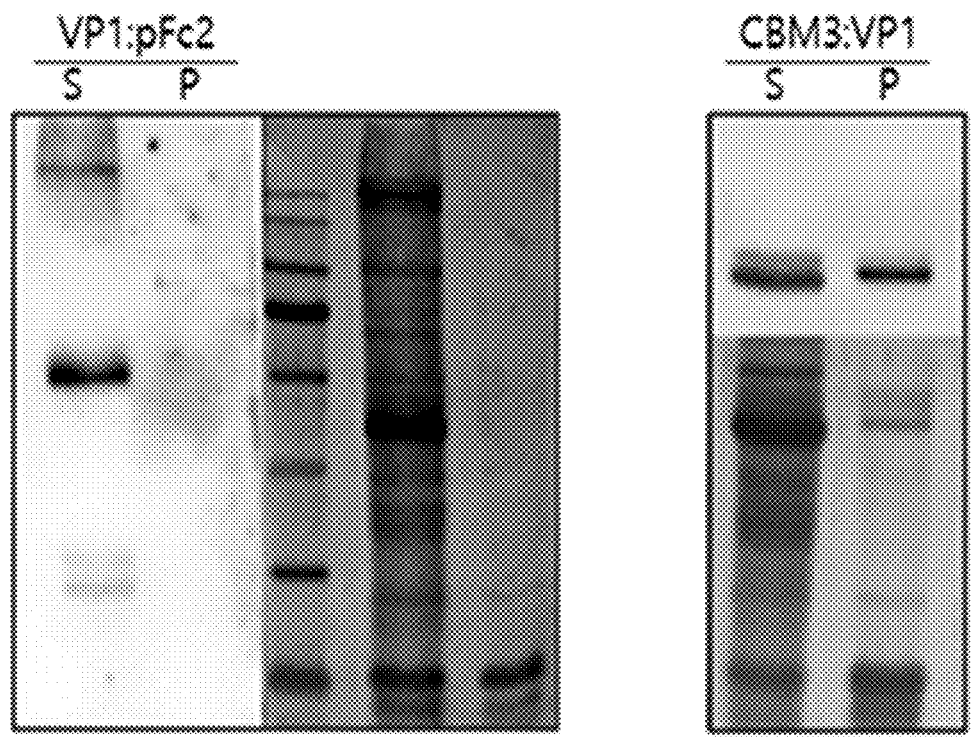
FIG. 5 is a view illustrating the result of confirming the solubility of a pFc fusion VP1 recombinant protein according to an embodiment of the present invention by western blotting.

As illustrated in FIG. 5, it was confirmed that the pFc2 fusion recombinant protein was not observed in the pellet part, whereas the pFc2 fusion recombinant protein was included in the solution. However, in the case of the recombinant protein fused with a cellulose binding domain, a considerable number of recombinant proteins were observed in the pellet part. Through the result, it could be confirmed that through the structural deformation caused by the binding of the target protein and the pFc fragment, the solubility of the pFc2 fusion recombinant protein was increased, and through this, it could be confirmed that the pFc2 fusion recombinant protein was advantageous in isolation and purification, and was effective for maintaining the physiological activity or pharmacological activity of the recombinant protein because the aggregation of the recombinant protein was suppressed.

Example 3: Experiment for Confirming Solubility of pFc2 Fusion GP5 Recombinant Antigen In order to fuse the pFc2 fragment with a GP5 antigen protein of Porcine reproductive and respiratory syndrome (PRRS), a recombinant vector expressing a GP5:pFc2 recombinant antigen was constructed by inserting a polynucleotide (SEQ ID No. 11) encoding a porcine GP5 antigen protein thereinto instead of the VP1 gene of the Foot-and-mouth disease virus included in the recombinant vector of Example 1. Next, after a pFc2 fusion GP5 recombinant antigen (GP5:pFc2) was expressed by a transient expression method for inoculating *Agrobacterium tumefaciens* transformed with the vector into leaves of a tobacco plant (*Nicotiana benthamiana*), a protein was extracted from the plant leaves and centrifuged, and then western blotting was performed in the same manner as in Example 2.1 using a protein in a soluble form (S) included in the solution and a protein present in the pellet (P) part. As a control, a GP5 recombinant antigen fused with CBM3 (SEQ ID No. 14) instead of the pFc fragment was used, and in the case of a CBM3 fusion GP5 recombinant antigen, an experiment was performed using an HA antibody for western blotting. The results are illustrated in FIG. 6.

Figure 6:
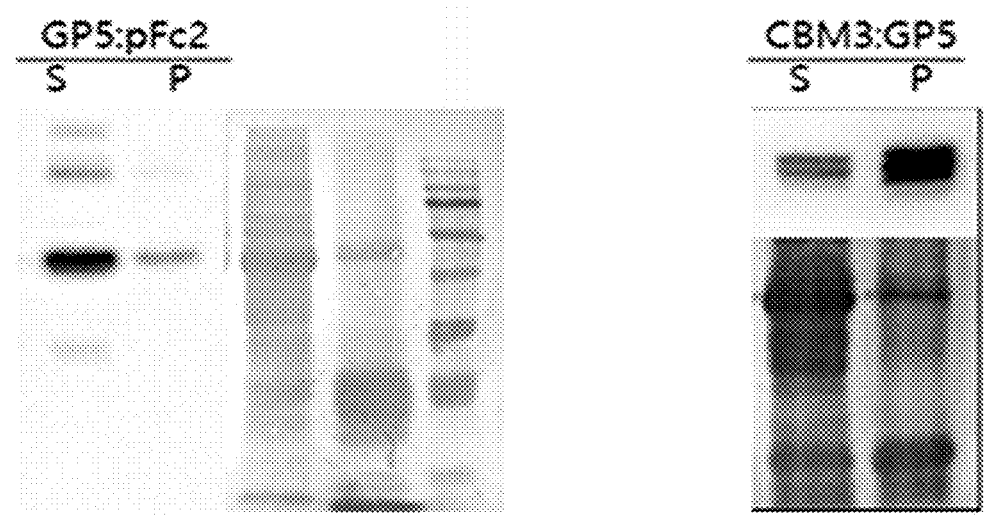
FIG. 6 is a view illustrating the result of confirming the solubility of a pFc fusion GP5 recombinant antigen according to an embodiment of the present invention by western blotting.

As illustrated in FIG. 6, it was confirmed that in the pFc2 fusion GP5 recombinant antigen, a small amount of protein was observed in the pellet part, whereas the pFc2 fusion GP5 recombinant antigen was mostly included in the solution. However, in the case of the GP5 recombinant antigen fused with CBM3, a considerable number of recombinant proteins were observed in the pellet part. Through the result, it could be confirmed that the pFc2 fusion recombinant protein had increased solubility regardless the type of protein.

Through the results, it could be confirmed that by fusing a porcine immunoglobulin Fc fragment, particularly, a pFc2 fragment including an amino acid sequence represented by SEQ ID No. 4 with a target protein, the expression level of the target protein was increased, and simultaneously, solubility was increased, thereby the target protein can be stably and easily isolated and stored.

Example 4: Experiment for Confirming Productivity and Solubility of pFc2 Fusion PCV2 Recombinant Protein In order to fuse the pFc2 fragment with a porcine circovirus type 2 (PCV2) protein, a recombinant vector expressing a PCV2:pFc2 recombinant protein was constructed by inserting a polynucleotide (SEQ ID No. 15) encoding the porcine circovirus type 2 protein thereinto instead of the VP1 gene of the Foot-and-mouth disease virus included in the recombinant vector of Example 1. Next, after the pFc2 fusion PCV2 recombinant protein was expressed by a transient expression method for inoculating Agrobacterium tumefaciens transformed with the vector into leaves of a tabacco plant (Nicotiana benthamiana), a protein was extracted from the plant leaves and centrifuged, and then western blotting was performed in the same manner as in Example 2.1 using a protein in a soluble form (S) included in the solution and a protein present in the pellet (P) part. As a control, a PCV2 recombinant protein fused with the His tag instead of the pFc fragment was used, and in the case of a His-tag fusion PCV2 recombinant protein, an experiment was performed using an anti-His antibody for western blotting. The results are illustrated in FIG. 7.

Figure 7:
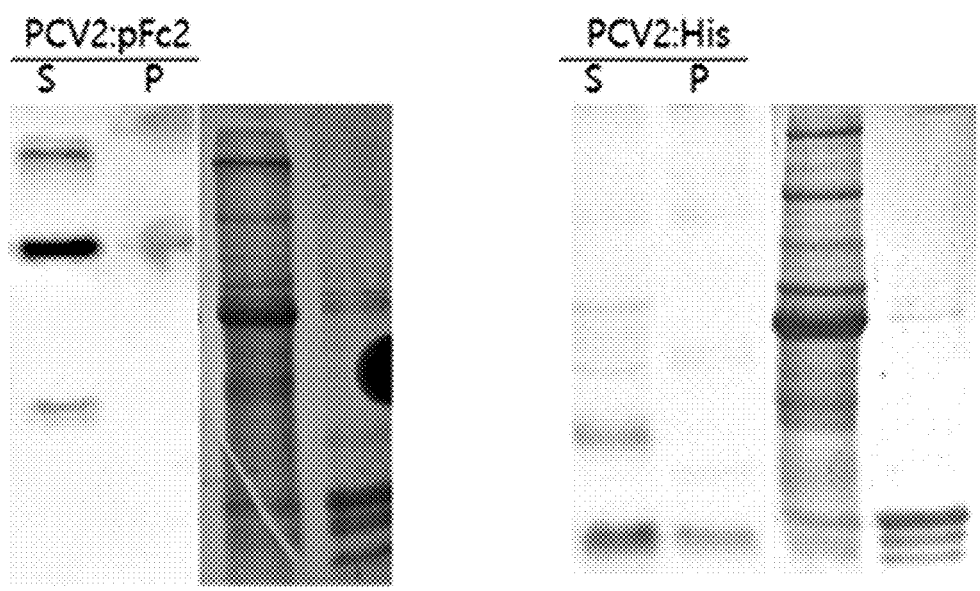
FIG. 7 is a view illustrating the result of confirming the solubility and productivity of a pFc fusion PCV2 recombinant protein according to an embodiment of the present invention by western blotting.

As illustrated in FIG. 7, it was confirmed that in the case of the pFc2 fusion PCV2 recombinant protein, not only most of the recombinant protein was included in the solution, but also the production amount was remarkably increased as compared to the His-tag-fused PCV2 recombinant protein.

Example 5: pFc2 Fusion E2 Recombinant Protein Expression Experiment 5.1. Isolation of pFc2 Fusion Antigen Protein In order to confirm whether the pFc2 fragment can be used by being fused with the antigen protein, a recombinant vector expressing a BiP:E2:pFc2 recombinant protein was constructed by inserting a polynucleotide (SEQ ID No. 17) encoding the E2 protein which is a classical swine fever antigen thereinto instead of the VP1 gene of the Foot-and-mouth disease virus included in the recombinant vector of Example 1. Next, a transformed plant body was prepared by transforming thale-cress with the prepared recombinant vector by Agrobacterium-mediated transformation, selecting thale-cress having resistance to kanamycin, and finally securing a homo seed in which the expression of an E2 recombinant protein fused with pFc2 was stabilized through generation advancement. Then, a protein was isolated from 8 g of the transformed plant body finally secured using a protein extraction buffer universally used for protein extraction, and a pFc fusion E2 recombinant protein was isolated using AKTA prime (GE Healthcare) equipped with a protein A-sepharose column. Next, as a control, a BiP:E2:CBD recombinant protein fused with a cellulose binding domain (SEQ ID No. 19) was used instead of the pFc fragment. The E2 recombinant protein fused with CBD was isolated from 5 g of the transformed plant body using amorphous cellulose (AMC). Next, the isolated recombinant protein was dialyzed using phosphate buffered saline (PBS), and then concentrated using a centrifugal filter tube. Next, in order to quantify the amount of the isolated recombinant protein, SDS-PAGE was performed, and then the isolated recombinant protein was stained with Coomassie blue. In this case, the recombinant protein was quantified using a standard curve using bovine serum albumin (BSA). The results are illustrated in FIG. 8.

Figure 8:
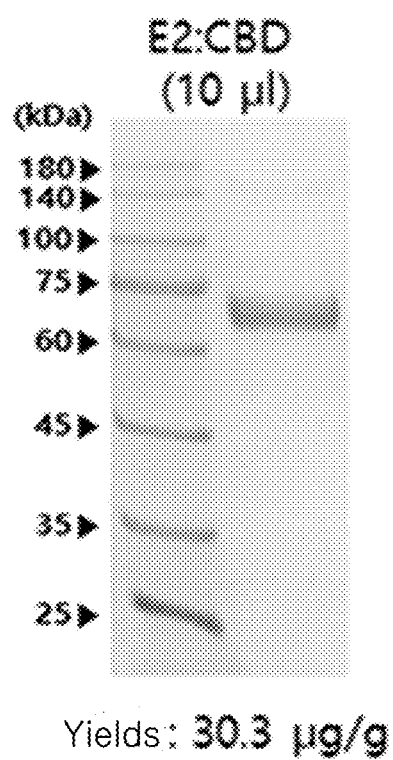
FIG. 8 is a view illustrating the result of confirming the production amount of a pFc fusion E2 recombinant antigen according to an embodiment of the present invention.
Figure 8:
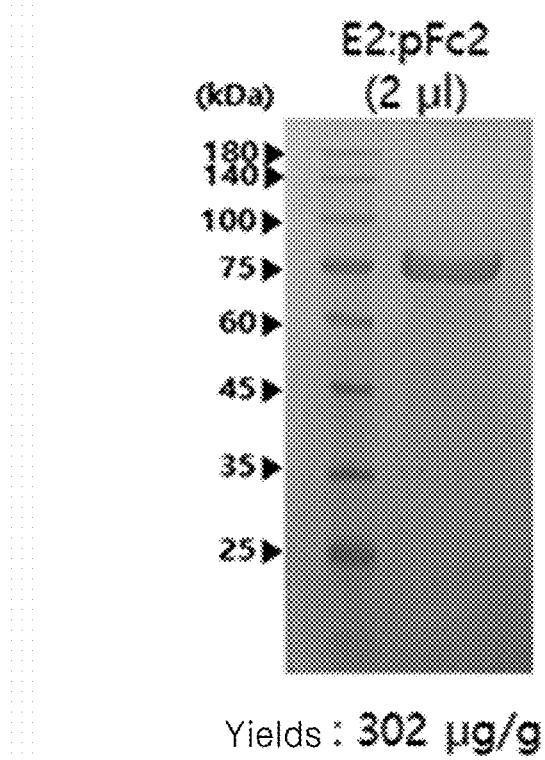

As illustrated in FIG. 8, it was confirmed that about 30 μg of the E2 recombinant antigen fused with the cellulose binding domain was produced per 1 g of the plant body, whereas 302 μg of the E2 recombinant antigen fused with the pFc2 fragment was produced per 1 g of the plant body. Through the result, it was confirmed that the expression level of the target antigen could be increased 10 fold or more using the pFc2 fragment.

5.2. Experiment for Confirming Immunogenicity and Virus Neutralization Ability of pFc2 Fusion E2 Recombinant Antigen In order to confirm whether the pFc fusion E2 recombinant antigen had immunogenicity and a virus neutralization ability by inducing an antibody in an organism, an experiment was performed using 6-week-old male C57BL/6J mice. More specifically, 1 μg of the pFc fusion E2 recombinant antigen was administered to the experimental group mice once (6 week old) or twice (6 week old and 8 week old), and a phosphate buffer solution was administered to the negative control mice. Also, as a positive control, the E2 recombinant antigen fused with the cellulose binding domain was administered in the same amount and at the same time as the experimental group. During each antigen administration, the same amount of Freund's adjuvant was mixed and administered. A complete adjuvant was administered to the one-time administration group. A complete adjuvant was administered at first-time administration, and then an incomplete adjuvant was administered at second-time administration to the two-time administration group. Also, at the time point when the experiment was started and from a week after the antigen was administered, the production of a specific antibody against an administered antigen and the persistence of the antibody were confirmed using an antibody kit for clinical diagnosis against the classical swine fever virus (CSFV-ab ELISA Kit, MEDIAN DIAGNOSTICS) by collecting blood every week. For the two-time administration group, blood collection was started one week after the completion of all the secondary administration. The experiment was performed using 5 mice in each group, and the results are shown in Table 1 and FIGS. 9 and 10. When the S/P value in Table 1 was 0.14 or more, the value was determined to be positive, and when the value was less than 0.14, the value was determined to be negative.

TABLE 1

| Ag | | 1 w | 2 w | 3 w | 4 w | 5 w | 6 w | 7 w | Fn. |
|---|---|---|---|---|---|---|---|---|---|
| E2:CBD | Mouse 1 | −0.10 | 0.33 | 0.69 | 1.04 | 1.58 | 1.42 | 1.62 | 1.26 |
| | Mouse 2 | −0.01 | 0.32 | 0.82 | 0.87 | 0.84 | 0.89 | 0.63 | 0.72 |
| | Mouse 3 | −0.07 | 0.90 | 0.89 | 0.80 | 0.85 | 1.21 | 1.41 | 1.47 |
| | Mouse 4 | −0.04 | 0.21 | 0.31 | 0.25 | 0.30 | 0.35 | 0.43 | 1.15 |
| | Mouse 5 | −0.07 | 0.14 | 0.31 | 0.46 | 0.74 | 0.96 | 1.08 | 0.96 |
| E2:pFc2 | Mouse 1 | 0.44 | 1.30 | 2.18 | 2.27 | 2.19 | 2.07 | 1.91 | 2.09 |
| | Mouse 2 | 1.15 | 1.75 | 2.65 | 3.14 | 3.23 | 2.82 | 2.87 | 2.80 |
| | Mouse 3 | 0.06 | 0.57 | 1.25 | 1.40 | 1.17 | 1.08 | 1.11 | 1.06 |
| | Mouse 4 | 0.40 | 1.72 | 2.66 | 2.59 | 2.58 | 2.55 | 2.49 | 3.10 |
| | Mouse 5 | 0.44 | 1.54 | 3.00 | 2.55 | 2.66 | 2.71 | 2.43 | 2.95 |

S/P value column header spans 1 w through Fn.

Figure 9:
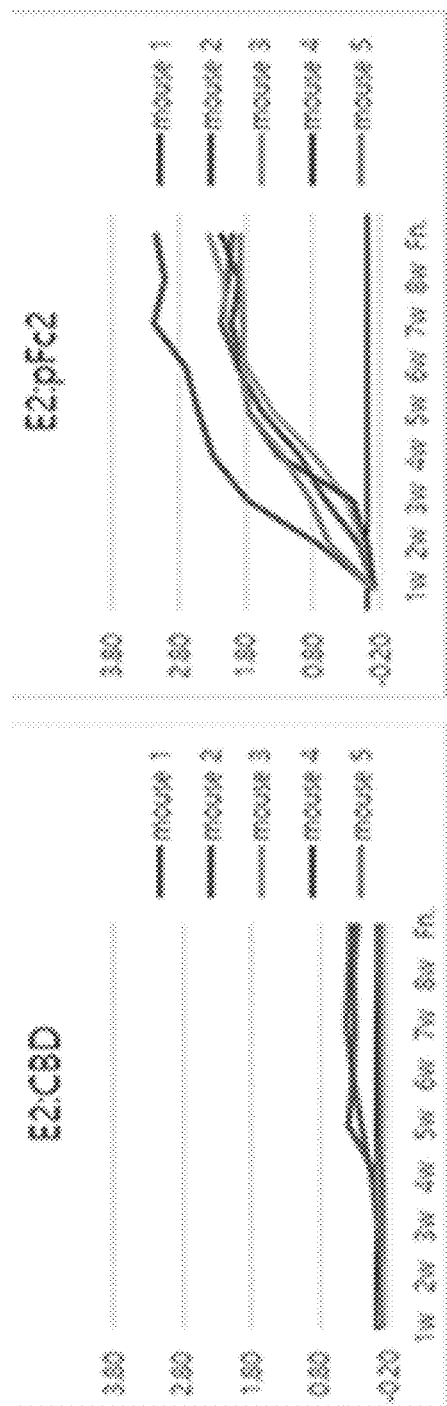
FIG. 9 is a view illustrating the result of administering a pFc fusion E2 recombinant antigen according to an embodiment of the present invention once and confirming immunogenicity.

As illustrated in FIG. 9, it was confirmed that when the antigen was administered once, the pFc2 fusion E2 recombinant antigen exhibited high reactivity from the time point when one week passed after the administration, and reactivity was maintained for 8 weeks or more. In contrast, it was confirmed that the E2 recombinant antigen fused with the cellulose binding domain exhibited positive values, but the reactivity thereof was lower than that of the pFc2 fusion E2 recombinant antigen.

Figure 10:
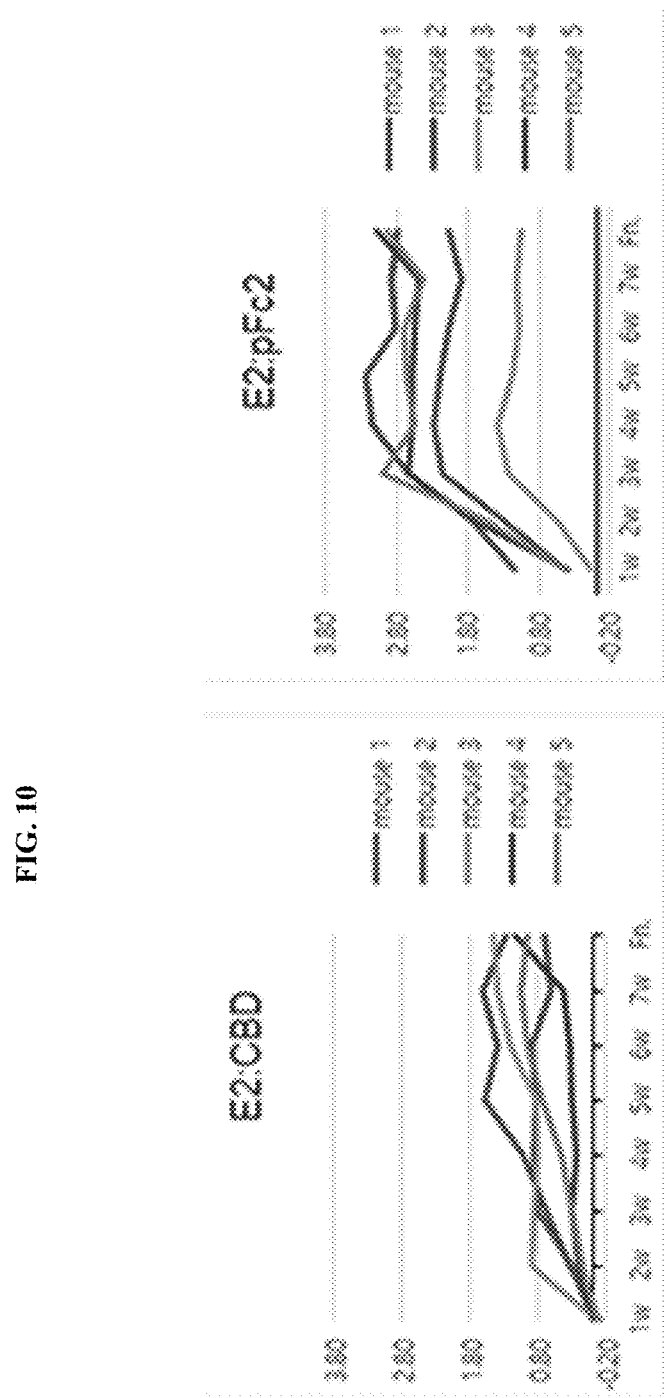
FIG. 10 is a view illustrating the result of administering a pFc fusion E2 recombinant antigen according to an embodiment of the present invention twice and confirming immunogenicity.

As illustrated in FIG. 10 and Table 1, it was confirmed that when the antigen was administered twice, even in the case of the E2 recombinant antigen fused with the cellulose binding domain, reactivity was increased as compared to when the antigen was administered once, but the reactivity was still low as compared to that of the pFc2 fusion E2 recombinant antigen.

Further, the Animal and Plant Quarantine Agency was requested to confirm the virus neutralization ability of the serum samples from the same mice. The results are shown in Table 2.

TABLE 2

| Experimental order | Antigen | Individual number | Neutralization antibody value |
|---|---|---|---|
| 2-1 order (Two-time injection) | E2: CBD | 1 | 64 |
| | | 2 | 32 |
| | | 3 | 32 |
| | | 4 | 32 |
| | | 5 | 128 |
| | E2: pFc2 | 1 | 128 |
| | | 2 | 256 |
| | | 3 | 32 |
| | | 4 | 256 |
| | | 5 | 512 |
| 2-2 order (One-time injection) | E2: CBD | 1 | 4 |
| | | 2 | 4 |
| | | 3 | <4 |
| | | 4 | <4 |
| | | 5 | <4 |
| | E2: pFc2 | 1 | 256 |
| | | 2 | 256 |
| | | 3 | 64 |
| | | 4 | 128 |
| | | 5 | 64 |
| Negative | | | <4 |
| Positive | | | 2048 |

As illustrated in Table 2, it was confirmed that the E2 recombinant antigen fused with the cellulose binding domain exhibited negative values in some mice when the antigen was administered once, but the pFc2 fusion E2 recombinant antigen exhibited a high titer of virus neutralization ability regardless of one-time administration or two-time administration.

5.3. Experiment for Confirming Virus Neutralization Ability of pFc2 Fusion E2 Recombinant Antigen In order to confirm whether the pFc2 fusion E2 recombinant antigen equally exhibited a high titer of virus neutralization ability even in a piglet, 4 classical swine fever antibody-negative pigs were selected and administered the pFc2 fusion E2 recombinant antigen twice, and the Animal and Plant Quarantine Agency was requested to confirm the virus neutralization ability in sera obtained at an interval of two weeks. The results are shown in Table 3.

TABLE 3

| Age | | Week 0 (Primary administration) | Week 2 (Secondary administration) | Week 4 | Week 6 | Week 8 | Week 10 | Week 12 |
|---|---|---|---|---|---|---|---|---|
| Each individual | | Neutralizing antibody | Neutralizing antibody | Neutralizing antibody | Neutralizing antibody | Neutralizing antibody | Neutralizing antibody | Neutralizing antibody |
| E2:pFc2 | #7 | 1 | <1 | 8 | 7 | 7 | 7 | 6 |
| | #8 | <1 | 1 | 9 | 8 | 7 | 8 | 6 |
| | #9 | <4 | 4 | 8 | 7 | 6 | 5 | 5 |
| | #10 | 2 | 4 | 10 | 9 | 7 | 7 | 6 |
| | Average | 1.5 | 2.25 | 8.75 | 7.75 | 6.75 | 6.75 | 5.75 |

As illustrated in Table 3, it was confirmed that all the piglets showed the positive value as in the experiment performed using the mice of Example 3.2.

Through the results, it could be confirmed that in the case of the recombinant antigen prepared by fusing the pFc2 fragment, the productivity of the antigen was increased, the immune response of the recombinant antigen was rapid, and reactivity was remarkably increased as compared to the existing cellulose fusion E2 recombinant antigen. Through the result, it could be confirmed that the pFc2 fragment exhibited an autoimmune-enhancing (self-adjuvanting) effect, and thus exhibited a self-adjuvant effect by fusing the pFc2 fragment with the existing antigen, thereby remarkably increasing the immunogenicity of a target antigen and improving productivity and stability. Furthermore, it could be confirmed that the pFc2 fusion E2 recombinant antigen could be used as a novel classical swine fever vaccine composition.

Hereinafter, the preparation examples of the pharmaceutical composition and feed composition of the present invention will be described, but the description is not intended to limit the present invention and is merely intended to describe the present invention in detail.

Preparation Example 1. Preparation of Pharmaceutical Composition 1.1. Preparation of Powder

| | |
|---|---|
| pFc2 fusion E2 recombinant antigen | 20 mg |
| Milk sugar | 100 mg |
| Talc | 10 mg |

A powder is prepared by mixing the ingredients and filling an airtight pack with the ingredients.

1.2. Preparation of Tablets

| | |
|---|---|
| pFc2 fusion E2 recombinant antigen | 10 mg |
| Corn starch | 100 mg |
| Milk sugar | 100 mg |
| Magnesium stearate | 2 mg |

After the ingredients are mixed, tablets are prepared by tableting the mixture according to a typical tablet preparation method.

1.3. Production of Capsules

| | |
|---|---|
| pFc2 fusion E2 recombinant antigen | 10 mg |
| Crystalline cellulose | 3 mg |
| Lactose | 14.8 mg |
| Magnesium stearate | 0.2 mg |

Capsules are prepared by mixing the ingredients according to a typical capsule preparation method and filling gelatin capsules with the mixture.

1.4. Preparation of Injection

| | |
|---|---|
| pFc2 fusion E2 recombinant antigen | 10 mg |
| Mannitol | 180 mg |
| Sterile distilled water for injection | 2,974 mg |
| $Na_2HPO_4 2H_2O$ | 26 mg |

According to the typical method for preparing an injection, an injection is prepared in a content of the ingredients per 1 ampoule (2 ml).

1.5. Preparation of Liquid

| | |
|---|---|
| pFc2 fusion E2 recombinant antigen | 20 mg |
| Isomerized sugar | 10 g |
| Mannitol | 5 g |
| Purified water | Appropriate amount |

In accordance with a typical method for preparing a liquid, each ingredient is added to purified water and dissolved, an appropriate amount of lemon flavor is added, and then the ingredients are mixed, and then purified water is added thereto and the total mixture is adjusted to 100 mL, and then a liquid is prepared by filling a brown bottle with the mixture and sterilizing the brown bottle.

Preparation Example 2. Preparation of Feed Composition

| | |
|---|---|
| pFc2 fusion E2 recombinant antigen | 100 mg |
| Vitamin E | 0.7 mg |
| L-carnitine | 0.7 mg |

In accordance with a typical method for preparing feed, feed is prepared by mixing the ingredients.

The above-described description of the present invention is provided for illustrative purposes, and the person skilled in the art to which the present invention pertains will understand that the present invention can be easily modified into other specific forms without changing the technical spirit or essential features of the present invention. Therefore, it should be understood that the above-described Examples are only exemplary in all aspects and are not restrictive.

INDUSTRIAL APPLICABILITY

Since the classical swine fever E2 protein fused with the porcine Fc fragment of the present invention can exhibit an autoimmune-enhancing effect, the solubility and stability of the antigen are enhanced to enhance the stability of the vaccine, and the production amount of the classical swine fever antigen E2 protein can be remarkably increased using the expression vector according to the present invention, the classical swine fever E2 protein is expected to be effectively used for production of a classical swine fever vaccine.

The invention claimed is:

1. A method for treating classical swine fever, comprising administering to a subject in need thereof a composition comprising a classical swine fever antigen E2 protein fused with a porcine Fc fragment consisting of the amino acid sequence of SEQ ID No. 4 as an active ingredient.

2. The method for treating classical swine fever of claim 1, wherein the E2 protein comprises the an amino acid sequence of SEQ ID No. 18.

3. The method for treating classical swine fever of claim 1, wherein the E2 protein is fused with the Fc fragment to have self-adjuvanting effect and increased solubility.

4. A recombinant vector for producing a classical swine fever antigen E2 protein fused with an Fc fragment, comprising a polynucleotide encoding a porcine Fc fragment consisting of the amino acid sequence of SEQ ID No. 4 and a polynucleotide encoding a classical swine fever antigen E2 protein.

5. The recombinant vector of claim 4, wherein the E2 protein comprises the amino acid sequence of SEQ ID No. 18.

6. The recombinant vector of claim 4, wherein the recombinant vector comprises a promoter gene operably and sequentially linked to the polynucleotide encoding a classical swine fever antigen E2 protein and the polynucleotide encoding a porcine Fc fragment.

7. The recombinant vector of claim 6, wherein the promoter is one or more selected from the group consisting of a cauliflower mosaic virus-derived 35S promoter, a cauliflower mosaic virus-derived 19S RNA promoter, an actin protein promoter of a plant, a ubiquitin protein promoter, a cytomegalovirus (CMV) promoter, a simian virus 40 (SV40) promoter, a respiratory syncytial virus (RSV) promoter, a pEMU promoter, an MAS promoter, a histone promoter, a Clp promoter, and an elongation factor-1 alpha (EF-1α) promoter.

8. The recombinant vector of claim 4, wherein the recombinant vector further comprises a polynucleotide encoding a chaperone binding protein (BiP).

9. The recombinant vector of claim 4, wherein the recombinant vector further comprises a gene encoding SEQ ID NO: 20.

10. The recombinant vector of claim 4, wherein the recombinant vector further comprises a 5' untranslated region (UTR) site gene of M17.

11. The recombinant vector of claim 4, wherein the recombinant vector increases an expression level of the classical swine fever antigen E2 protein fused with the Fc fragment.

12. A transgenic organism transformed with the recombinant vector of claim 4.

13. A method for producing a classical swine fever antigen E2 protein fused with an Fc fragment and having an autoimmune-enhancing effect, the method comprising:
    (a) culturing a transgenic organism transformed with the recombinant vector of claim 4; and
    (b) isolating a classical swine fever E2 protein fused with an Fc fragment from the transgenic organism or culture solution and purifying the classical swine fever E2 protein fused with the Fc fragment.

14. The recombinant vector of claim 4, wherein the E2 protein is fused with the Fc fragment to have self-adjuvanting effect and increased solubility.

* * * * *

SEQUENCE LISTING

<160> NUMBER OF SEQ ID NOS: 20

<210> SEQ ID NO 1
<211> LENGTH: 690
<212> TYPE: DNA
<213> ORGANISM: Artificial Sequence
<220> FEATURE:
<223> OTHER INFORMATION: DNA sequence of pFc1

<400> SEQUENCE: 1

```
ggaactaaga ctaagccacc ttgtcctatt tgtccagggt gcgaggtagc cggtcccagc    60
gtgtttattt ttccaccaaa accaaaggat actttgatga tatctcaaac accggaagtt   120
acttgcgttg tggtcgacgt ttcaaagag catgccgaag ttcagttctc ttggtatgtg    180
gatggtgtgg aagtgcacac cgctgagaca cgtcctaaag aggaacagtt taactctact   240
tacagagtcg tgtccgtatt gcccattcag catcaagact ggcttaaggg aaaagaattt   300
aaatgtaagg taaataatgt tgatctgcca gcacctataa ctagaaccat ctcgaaagct   360
attggacaat ctagagaacc tcaagtttat acattgcctc ctccagctga ggaactttct   420
agaagtaaag tcactgttac atgcttagtt attggattct atccaccaga tatccatgtt   480
gaatggaaat caaatggtca gcccgaacct gagggcaact acagaacaac accaccacag   540
caagatgtag atggtacttt tttcctctac tcaaaactag ctgttgataa ggctaggtgg   600
gatcatggcg agacatttga gtgtgcagtc atgcacgaag cacttcataa tcactatacc   660
caaaagtcca taagtaagac gcaaggaaag                                    690
```

<210> SEQ ID NO 2
<211> LENGTH: 230
<212> TYPE: PRT
<213> ORGANISM: Artificial Sequence
<220> FEATURE:
<223> OTHER INFORMATION: Amino acid sequence of pFc1

<400> SEQUENCE: 2

Gly Thr Lys Thr Lys Pro Pro Cys Pro Ile Cys Pro Gly Cys Glu Val
1               5                   10                  15

Ala Gly Pro Ser Val Phe Ile Phe Pro Pro Lys Pro Lys Asp Thr Leu
            20                  25                  30

Met Ile Ser Gln Thr Pro Glu Val Thr Cys Val Val Val Asp Val Ser
        35                  40                  45

Lys Glu His Ala Glu Val Gln Phe Ser Trp Tyr Val Asp Gly Val Glu
    50                  55                  60

Val His Thr Ala Glu Thr Arg Pro Lys Glu Glu Gln Phe Asn Ser Thr
65                  70                  75                  80

Tyr Arg Val Val Ser Val Leu Pro Ile Gln His Gln Asp Trp Leu Lys
                85                  90                  95

Gly Lys Glu Phe Lys Cys Lys Val Asn Asn Val Asp Leu Pro Ala Pro
            100                 105                 110

Ile Thr Arg Thr Ile Ser Lys Ala Ile Gly Gln Ser Arg Glu Pro Gln
        115                 120                 125

Val Tyr Thr Leu Pro Pro Pro Ala Glu Glu Leu Ser Arg Ser Lys Val
    130                 135                 140

Thr Val Thr Cys Leu Val Ile Gly Phe Tyr Pro Pro Asp Ile His Val
145                 150                 155                 160

Glu Trp Lys Ser Asn Gly Gln Pro Glu Pro Glu Gly Asn Tyr Arg Thr
                165                 170                 175

Thr Pro Pro Gln Gln Asp Val Asp Gly Thr Phe Phe Leu Tyr Ser Lys
            180                 185                 190

Leu Ala Val Asp Lys Ala Arg Trp Asp His Gly Glu Thr Phe Glu Cys
        195                 200                 205

Ala Val Met His Glu Ala Leu His Asn His Tyr Thr Gln Lys Ser Ile

Ser Lys Thr Gln Gly Lys
225                 230

<210> SEQ ID NO 3
<211> LENGTH: 681
<212> TYPE: DNA
<213> ORGANISM: Artificial Sequence
<220> FEATURE:
<223> OTHER INFORMATION: DNA sequence of pFc2

<400> SEQUENCE: 3

```
gttggaagac catgccctat atgtcctgct tgtgaaggtc caggtccctc tgcttttata      60
ttcccaccaa agccgaagga taccttgatg atttcacgta caccacaagt tacttgtgtt     120
gttgtggatg tttcacaaga aaatcctgag gtacaattca gctggtatgt tgatggggta     180
gaagtgcaca ctgcacagac tcgaccaaag gaggcccagt taactcgac ttatagagtt      240
gtttctgttc tcccaatcca acacgaagat tggctgaagg caaggaatt tgaatgcaag      300
gttaacaata aagatctacc agcaccaatt accaggatta tttctaaggc aaaaggaccc     360
tccagagagc cccaagttta cacattgtct ccttctgctg aggagcttag tagaagtaaa     420
gtgagcatta cctgcttagt gacgggattc taccctccag acatcgacgt cgaatggaaa     480
tctaatggtc aacctgagcc agaaggtaac tataggacta ctccaccaca acaggacgtc     540
gatggcacat actttcttta ttcaaaactt gctgtcgata aggcaagttg gcaaagagga     600
gatccatttc agtgtgctgt aatgcatgag gctttgcata atcattatac acagaaatca     660
gtttctaaaa cacaagggaa a                                                681
```

<210> SEQ ID NO 4
<211> LENGTH: 227
<212> TYPE: PRT
<213> ORGANISM: Artificial Sequence
<220> FEATURE:
<223> OTHER INFORMATION: Amino acid sequence of pFc2

<400> SEQUENCE: 4

Val Gly Arg Pro Cys Pro Ile Cys Pro Ala Cys Glu Gly Pro Gly Pro
1               5                   10                  15

Ser Ala Phe Ile Phe Pro Pro Lys Pro Lys Asp Thr Leu Met Ile Ser
            20                  25                  30

Arg Thr Pro Gln Val Thr Cys Val Val Val Asp Val Ser Gln Glu Asn
        35                  40                  45

Pro Glu Val Gln Phe Ser Trp Tyr Val Asp Gly Val Glu Val His Thr
    50                  55                  60

Ala Gln Thr Arg Pro Lys Glu Ala Gln Phe Asn Ser Thr Tyr Arg Val
65                  70                  75                  80

Val Ser Val Leu Pro Ile Gln His Glu Asp Trp Leu Lys Gly Lys Glu
                85                  90                  95

Phe Glu Cys Lys Val Asn Asn Lys Asp Leu Pro Ala Pro Ile Thr Arg
            100                 105                 110

Ile Ile Ser Lys Ala Lys Gly Pro Ser Arg Glu Pro Gln Val Tyr Thr
        115                 120                 125

Leu Ser Pro Ser Ala Glu Glu Leu Ser Arg Ser Lys Val Ser Ile Thr
    130                 135                 140

Cys Leu Val Thr Gly Phe Tyr Pro Pro Asp Ile Asp Val Glu Trp Lys
145                 150                 155                 160

-continued

Ser Asn Gly Gln Pro Glu Pro Glu Gly Asn Tyr Arg Thr Thr Pro Pro
            165                 170                 175

Gln Gln Asp Val Asp Gly Thr Tyr Phe Leu Tyr Ser Lys Leu Ala Val
        180                 185                 190

Asp Lys Ala Ser Trp Gln Arg Gly Asp Pro Phe Gln Cys Ala Val Met
    195                 200                 205

His Glu Ala Leu His Asn His Tyr Thr Gln Lys Ser Val Ser Lys Thr
210                 215                 220

Gln Gly Lys
225

<210> SEQ ID NO 5
<211> LENGTH: 702
<212> TYPE: DNA
<213> ORGANISM: Artificial Sequence
<220> FEATURE:
<223> OTHER INFORMATION: DNA sequence of pFc3

<400> SEQUENCE: 5
attgagccac cgacacctat ttgtcctgaa atatgctctt gccctgcggc cgaagtttta      60
ggagcaccgt cggtctttct gtttccacct aaacctaagg acattttaat gatctctagg     120
acgcccaagg taacttgtgt tgttgttgat gtttctcaag aagaagctga ggttcaattc     180
tcctggtatg tagacggcgt tcaattgtac accgcacaga ctaggcctat ggaagaacag     240
tttaactcaa catacagagt agtgtccgtg ttgccgatcc aacatcaaga ttggttgaaa     300
ggtaaagagt ttaagtgtaa agtgaacaat aaggatctcc tttctcctat taccagaact     360
ataagtaaag ctaccggacc atctcgggtt ccacaggtct acactcttcc accagcttgg     420
gaggagctta gcaagtcaaa ggtaagcatc acttgtctcg taacgggatt ctatccacca     480
gatattgatg tggaatggca gagtaatggt caacaggaac ccgagggtaa ttaccgaaca     540
actcctcctc agcaggatgt tgacggtact tattttcttt attcaaagct agctgttgat     600
aaagtgagat ggcaacgtgg cgatttgttc cagtgcgcag tcatgcatga ggctcttcat     660
aatcactata cacaaaaatc aatttctaag acacaaggga ag                        702

<210> SEQ ID NO 6
<211> LENGTH: 234
<212> TYPE: PRT
<213> ORGANISM: Artificial Sequence
<220> FEATURE:
<223> OTHER INFORMATION: Amino acid sequence of pFc3

<400> SEQUENCE: 6

Ile Glu Pro Pro Thr Pro Ile Cys Pro Glu Ile Cys Ser Cys Pro Ala
1               5                   10                  15

Ala Glu Val Leu Gly Ala Pro Ser Val Phe Leu Phe Pro Pro Lys Pro
            20                  25                  30

Lys Asp Ile Leu Met Ile Ser Arg Thr Pro Lys Val Thr Cys Val Val
        35                  40                  45

Val Asp Val Ser Gln Glu Glu Ala Glu Val Gln Phe Ser Trp Tyr Val
    50                  55                  60

Asp Gly Val Gln Leu Tyr Thr Ala Gln Thr Arg Pro Met Glu Glu Gln
65                  70                  75                  80

Phe Asn Ser Thr Tyr Arg Val Val Ser Val Leu Pro Ile Gln His Gln
                85                  90                  95

Asp Trp Leu Lys Gly Lys Glu Phe Lys Cys Lys Val Asn Asn Lys Asp
            100                 105                 110

-continued

```
Leu Leu Ser Pro Ile Thr Arg Thr Ile Ser Lys Ala Thr Gly Pro Ser
        115                 120                 125

Arg Val Pro Gln Val Tyr Thr Leu Pro Pro Ala Trp Glu Glu Leu Ser
    130                 135                 140

Lys Ser Lys Val Ser Ile Thr Cys Leu Val Thr Gly Phe Tyr Pro Pro
145                 150                 155                 160

Asp Ile Asp Val Glu Trp Gln Ser Asn Gly Gln Gln Glu Pro Glu Gly
                165                 170                 175

Asn Tyr Arg Thr Thr Pro Pro Gln Gln Asp Val Asp Gly Thr Tyr Phe
            180                 185                 190

Leu Tyr Ser Lys Leu Ala Val Asp Lys Val Arg Trp Gln Arg Gly Asp
        195                 200                 205

Leu Phe Gln Cys Ala Val Met His Glu Ala Leu His Asn His Tyr Thr
    210                 215                 220

Gln Lys Ser Ile Ser Lys Thr Gln Gly Lys
225                 230

<210> SEQ ID NO 7
<211> LENGTH: 21
<212> TYPE: DNA
<213> ORGANISM: Artificial Sequence
<220> FEATURE:
<223> OTHER INFORMATION: 5'UTR of M17 gene

<400> SEQUENCE: 7
ggcgtgtgtg tgtgttaaag a                                                21

<210> SEQ ID NO 8
<211> LENGTH: 272
<212> TYPE: DNA
<213> ORGANISM: Artificial Sequence
<220> FEATURE:
<223> OTHER INFORMATION: DNA sequence of chapherone binding protein(BiP)

<400> SEQUENCE: 8
atggctcgct cgtttggagc taacagtacc gttgtgttgg cgatcatctt cttcggtgag      60
tgattttccg atcttcttct ccgatttaga tctcctctac attgttgctt aatctcagaa     120 cctttttttcg ttgttcctgg atctgaatgt gtttgtttgc aatttcacga tcttaaaagg     180
ttagatctcg attggtattg acgattggaa tctttacgat ttcaggatgt ttatttgcgt     240
tgtcctctgc aatagaagag gctacgaagt ta                                   272

<210> SEQ ID NO 9
<211> LENGTH: 639
<212> TYPE: DNA
<213> ORGANISM: Artificial Sequence
<220> FEATURE:
<223> OTHER INFORMATION: DNA sequence of FMDV-VP1

<400> SEQUENCE: 9
actacaagta ccggcgaatc tgctgatcca gttactgcta cagttgaaaa ttatggtgga      60
gaaacacaag tgcaaagaag acatcataca gatgtttctt ttatcctaga taggtttgtt     120
aaggtcactc ctaaggattc aattaatgtt ttggacctga tgcagactcc cccacataca     180
ttggttggcg ctctacttcg tactgcaact tattatttcg ctgatttaga ggtagccgtt     240
aaacacgaag gtgatttaac atgggttcct aatggagcac ctgaggctgc actcgataat     300
actactaatc caactgctta ccacaaagca ccactcacta gactcgcgct tccttacact     360
```

```
gccccgcata gggttcttgc tactgtttat aacgggaact gcaaatacgc aggtggttca      420
ttgcctaatg tacgaggaga tttgcaagta ttggctcaaa aagcagcatg gccattacct      480
acttctttta actatggagc tataaaggct acacgtgtga cggaacttct ttataggatg      540
aagagagctg agacatactg tcctagacca ttactggctg ttcatccatc cgccgcaaga      600
cacaaacaga aaattgtggc tcccgttaag cagagccctt                            639
```

<210> SEQ ID NO 10
<211> LENGTH: 213
<212> TYPE: PRT
<213> ORGANISM: Artificial Sequence
<220> FEATURE:
<223> OTHER INFORMATION: Amino acid sequence of FMDV-VP1

<400> SEQUENCE: 10

```
Thr Thr Ser Thr Gly Glu Ser Ala Asp Pro Val Thr Ala Thr Val Glu
1               5                   10                  15

Asn Tyr Gly Gly Glu Thr Gln Val Gln Arg Arg His His Thr Asp Val
            20                  25                  30

Ser Phe Ile Leu Asp Arg Phe Val Lys Val Thr Pro Lys Asp Ser Ile
        35                  40                  45

Asn Val Leu Asp Leu Met Gln Thr Pro Pro His Thr Leu Val Gly Ala
    50                  55                  60

Leu Leu Arg Thr Ala Thr Tyr Tyr Phe Ala Asp Leu Glu Val Ala Val
65                  70                  75                  80

Lys His Glu Gly Asp Leu Thr Trp Val Pro Asn Gly Ala Pro Glu Ala
                85                  90                  95

Ala Leu Asp Asn Thr Thr Asn Pro Thr Ala Tyr His Lys Ala Pro Leu
            100                 105                 110

Thr Arg Leu Ala Leu Pro Tyr Thr Ala Pro His Arg Val Leu Ala Thr
        115                 120                 125

Val Tyr Asn Gly Asn Cys Lys Tyr Ala Gly Gly Ser Leu Pro Asn Val
    130                 135                 140

Arg Gly Asp Leu Gln Val Leu Ala Gln Lys Ala Ala Trp Pro Leu Pro
145                 150                 155                 160

Thr Ser Phe Asn Tyr Gly Ala Ile Lys Ala Thr Arg Val Thr Glu Leu
                165                 170                 175

Leu Tyr Arg Met Lys Arg Ala Glu Thr Tyr Cys Pro Arg Pro Leu Leu
            180                 185                 190

Ala Val His Pro Ser Ala Ala Arg His Lys Gln Lys Ile Val Ala Pro
        195                 200                 205

Val Lys Gln Ser Leu
    210
```

<210> SEQ ID NO 11
<211> LENGTH: 330
<212> TYPE: DNA
<213> ORGANISM: Artificial Sequence
<220> FEATURE:
<223> OTHER INFORMATION: DNA sequence for GP5

<400> SEQUENCE: 11

```
aacggcaaca gctcgacata ccaatacata taaacttga cggtatgcga gctgaatggg       60
accgcctggt tgtctaccca cttttcttgg gcagtcgaga ccggaggcgg gggtagcaaa      120
aattgtatgg cttgccgcta cgcccgcacc cggttcacca acttcattgt agacgaccgg      180
gggaggattc atcggtggaa gtccccggtg gtggtggaga aatttggcaa agccgaaatt      240
```
ggcggcggtc ttgtcaccat caaacatgtc gtcctcgaag gggttaaagc tcaacccttg    300
acgaggactt cggctgagca atgggaagcc                                    330

<210> SEQ ID NO 12
<211> LENGTH: 110
<212> TYPE: PRT
<213> ORGANISM: Artificial Sequence
<220> FEATURE:
<223> OTHER INFORMATION: Amino acid sequence for GP5

<400> SEQUENCE: 12

Asn Gly Asn Ser Ser Thr Tyr Gln Tyr Ile Tyr Asn Leu Thr Val Cys
1               5                   10                  15

Glu Leu Asn Gly Thr Ala Trp Leu Ser Thr His Phe Ser Trp Ala Val
            20                  25                  30

Glu Thr Gly Gly Gly Gly Ser Lys Asn Cys Met Ala Cys Arg Tyr Ala
        35                  40                  45

Arg Thr Arg Phe Thr Asn Phe Ile Val Asp Asp Arg Gly Arg Ile His
    50                  55                  60

Arg Trp Lys Ser Pro Val Val Glu Lys Phe Gly Lys Ala Glu Ile
65                  70                  75                  80

Gly Gly Gly Leu Val Thr Ile Lys His Val Val Leu Glu Gly Val Lys
                85                  90                  95

Ala Gln Pro Leu Thr Arg Thr Ser Ala Glu Gln Trp Glu Ala
            100                 105                 110

<210> SEQ ID NO 13
<211> LENGTH: 477
<212> TYPE: DNA
<213> ORGANISM: Artificial Sequence
<220> FEATURE:
<223> OTHER INFORMATION: DNA sequence for CBM3

<400> SEQUENCE: 13
gtatcaggta accttaaggt ggagttttac aactcgaacc cttctgatac aactaactca     60
ataaacccac agttcaaagt tacaaacaca ggcagctctg cgatcgattt gtctaaatta    120
accctcagat actattatac ggttgatgga cagaaggacc agactttctg gtgtgatcat    180
gcagctatca ttggttctaa cggtagctac aacggaatta catcaaacgt gaagggcact    240
ttcgttaaga tgtcctctag cactaacaac gcagacacat atttggagat cagttttacg    300
gggggaaccc ttgaaccagg tgctcacgtc cagattcaag gaagattcgc taaaaacgac    360
tggtcgaact atacccaaag taatgattac agttttaaat ccgcctcaca atttgttgag    420
tgggatcagg tcactgctta cctgaacggg gttctagtgt ggggaaagga acctggt      477

<210> SEQ ID NO 14
<211> LENGTH: 159
<212> TYPE: PRT
<213> ORGANISM: Artificial Sequence
<220> FEATURE:
<223> OTHER INFORMATION: Amino acid sequence for CBM3

<400> SEQUENCE: 14

Val Ser Gly Asn Leu Lys Val Glu Phe Tyr Asn Ser Asn Pro Ser Asp
1               5                   10                  15

Thr Thr Asn Ser Ile Asn Pro Gln Phe Lys Val Thr Asn Thr Gly Ser
            20                  25                  30

Ser Ala Ile Asp Leu Ser Lys Leu Thr Leu Arg Tyr Tyr Tyr Thr Val

```
                35                  40                  45
Asp Gly Gln Lys Asp Gln Thr Phe Trp Cys Asp His Ala Ala Ile Ile
 50                  55                  60
Gly Ser Asn Gly Ser Tyr Asn Gly Ile Thr Ser Asn Val Lys Gly Thr
65                  70                  75                  80
Phe Val Lys Met Ser Ser Thr Asn Asn Ala Asp Thr Tyr Leu Glu
                85                  90                  95
Ile Ser Phe Thr Gly Gly Thr Leu Glu Pro Gly Ala His Val Gln Ile
                100                 105                 110
Gln Gly Arg Phe Ala Lys Asn Asp Trp Ser Asn Tyr Thr Gln Ser Asn
                115                 120                 125
Asp Tyr Ser Phe Lys Ser Ala Ser Gln Phe Val Glu Trp Asp Gln Val
130                 135                 140
Thr Ala Tyr Leu Asn Gly Val Leu Val Trp Gly Lys Glu Pro Gly
145                 150                 155
```

<210> SEQ ID NO 15
<211> LENGTH: 579
<212> TYPE: DNA
<213> ORGANISM: Artificial Sequence
<220> FEATURE:
<223> OTHER INFORMATION: DNA sequence for PCV2

<400> SEQUENCE: 15

```
aaaaatggca ttttcaatac acgcctcagt cgaacttttg atatactgtc aagcgtact    60
acagtcacca cgccatcttg ggctgtggat atgatgagat taagttggat gactttgtt   120
cctcctggag ggggaaccaa caaaatttct ataccgtttg agtactatag aatcagaaaa  180
gttaaggttg agttctggcc gtgttccccc ataactcagg gtgataggg tgtgggttca   240
actgctgtta ttctagatga taacttcgta cctaaggcca acgcattgac ttatgacccc  300
tatgtaaact actcatctag acatacaatc ccacaacctt ctcctacca ctcgcgttat   360
tttacaccaa agcctgtttt agattctacc attgattatt ccaaccaaa taacaagagg   420
aatcagcttt ggttgagatt acaaacctca cggaacgtgg atcatgtcgg attgggtact  480
gcatttgaaa atagtaagta tgatcaggac tacaatatcc gtgtgacaat gtacgttcaa  540
tttagggaat ttaatcttaa agacccacca cttaatcca                        579
```

<210> SEQ ID NO 16
<211> LENGTH: 193
<212> TYPE: PRT
<213> ORGANISM: Artificial Sequence
<220> FEATURE:
<223> OTHER INFORMATION: Amino acid sequence for PCV2

<400> SEQUENCE: 16

```
Lys Asn Gly Ile Phe Asn Thr Arg Leu Ser Arg Thr Phe Gly Tyr Thr
1               5                  10                  15
Val Lys Arg Thr Thr Val Thr Pro Ser Trp Ala Val Asp Met Met
                20                  25                  30
Arg Phe Lys Leu Asp Asp Phe Val Pro Pro Gly Gly Gly Thr Asn Lys
                35                  40                  45
Ile Ser Ile Pro Phe Glu Tyr Tyr Arg Ile Arg Lys Val Lys Val Glu
                50                  55                  60
Phe Trp Pro Cys Ser Pro Ile Thr Gln Gly Asp Arg Gly Val Gly Ser
65                  70                  75                  80
Thr Ala Val Ile Leu Asp Asp Asn Phe Val Pro Lys Ala Asn Ala Leu
```

```
              85                  90                  95
Thr Tyr Asp Pro Tyr Val Asn Tyr Ser Ser Arg His Thr Ile Pro Gln
              100                 105                 110

Pro Phe Ser Tyr His Ser Arg Tyr Phe Thr Pro Lys Pro Val Leu Asp
          115                 120                 125

Ser Thr Ile Asp Tyr Phe Gln Pro Asn Asn Lys Arg Asn Gln Leu Trp
      130                 135                 140

Leu Arg Leu Gln Thr Ser Arg Asn Val Asp His Val Gly Leu Gly Thr
145                 150                 155                 160

Ala Phe Glu Asn Ser Lys Tyr Asp Gln Asp Tyr Asn Ile Arg Val Thr
                165                 170                 175

Met Tyr Val Gln Phe Arg Glu Phe Asn Leu Lys Asp Pro Pro Leu Asn
            180                 185                 190

Pro

<210> SEQ ID NO 17
<211> LENGTH: 1026
<212> TYPE: DNA
<213> ORGANISM: Artificial Sequence
<220> FEATURE:
<223> OTHER INFORMATION: DNA sequence of E2

<400> SEQUENCE: 17
aacggctagc ctgcaaggaa gattacaggt acgcaatatc atcaaccaat gagatagggc      60
tactcggggc cggaggtctc accaccacct ggaaagaata caaccacgat ttgcaactga     120
atgacgggac cgttaaggcc atttgcgtgg caggttcctt taaagtcaca gcacttaatg     180
tggtcagtag gaggtatttg gcatcattgc ataaggaggc tttacccact tccgtgacat     240
tcgagctcct gttcgacggg accaacccat caactgagga aatgggagat gacttcgggt     300
tcgggctgtg cccgtttgat acgagtcctg ttgtcaaagg aaagtacaat acaaccttgt     360
tgaacggtag tgctttctat cttgtctgtc aatagggtg gacgggtgtt atagagtgca     420
cagcagtgag cccaacaact ctgagaacag aagtggtaaa gaccttcagg agggacaagc     480
cctttccgca cagaatggat tgtgtgacca acagtggaa aaatgaagat ttattctact     540
gtaagttggg gggcaactgg acatgtgtga aggtgaacc agtggtctac acggggggc     600 tagtaaaaca atgcagatgg tgtggctttg acttcaatga gcctgacgga ctcccacact     660
accccatagg taagtgcatt ttggcaaatg agacaggtta cagaatagtg gattcaacag     720
actgtaacag agatggtgtt gtaatcagca cagaggggag tcatgagtgc ttgatcggta     780
acacgactgt caaggtgcat gcatcagatg aaagactggg ccccatgcca tgcagaccta     840
aagagatcgt ctctagtgca ggacctgtaa ggaaaacttc ctgtacattc aactacgcaa     900
aaactttgaa gaacaagtac tatgagccca gggacagcta cttccagcaa tatatgctta     960
agggcgagta tcagtactgg tttgacctgg acgtgactga ccgccactca gattacttcg    1020
cagaag                                                                1026

<210> SEQ ID NO 18
<211> LENGTH: 341
<212> TYPE: PRT
<213> ORGANISM: Artificial Sequence
<220> FEATURE:
<223> OTHER INFORMATION: Amino acid sequence of E2

<400> SEQUENCE: 18

Arg Leu Ala Cys Lys Glu Asp Tyr Arg Tyr Ala Ile Ser Ser Thr Asn
```

```
  1               5                   10                  15
Glu Ile Gly Leu Leu Gly Ala Gly Gly Leu Thr Thr Thr Trp Lys Glu
            20                  25                  30

Tyr Asn His Asp Leu Gln Leu Asn Asp Gly Thr Val Lys Ala Ile Cys
            35                  40                  45

Val Ala Gly Ser Phe Lys Val Thr Ala Leu Asn Val Val Ser Arg Arg
 50                  55                  60

Tyr Leu Ala Ser Leu His Lys Glu Ala Leu Pro Thr Ser Val Thr Phe
 65                  70                  75                  80

Glu Leu Leu Phe Asp Gly Thr Asn Pro Ser Thr Glu Glu Met Gly Asp
                85                  90                  95

Asp Phe Gly Phe Gly Leu Cys Pro Phe Asp Thr Ser Pro Val Val Lys
                100                 105                 110

Gly Lys Tyr Asn Thr Thr Leu Leu Asn Gly Ser Ala Phe Tyr Leu Val
            115                 120                 125

Cys Pro Ile Gly Trp Thr Gly Val Ile Glu Cys Thr Ala Val Ser Pro
            130                 135                 140

Thr Thr Leu Arg Thr Glu Val Val Lys Thr Phe Arg Arg Asp Lys Pro
145                 150                 155                 160

Phe Pro His Arg Met Asp Cys Val Thr Thr Val Glu Asn Glu Asp
                165                 170                 175

Leu Phe Tyr Cys Lys Leu Gly Gly Asn Trp Thr Cys Val Lys Gly Glu
            180                 185                 190

Pro Val Val Tyr Thr Gly Gly Leu Val Lys Gln Cys Arg Trp Cys Gly
            195                 200                 205

Phe Asp Phe Asn Glu Pro Asp Gly Leu Pro His Tyr Pro Ile Gly Lys
 210                 215                 220

Cys Ile Leu Ala Asn Glu Thr Gly Tyr Arg Ile Val Asp Ser Thr Asp
225                 230                 235                 240

Cys Asn Arg Asp Gly Val Val Ile Ser Thr Glu Gly Ser His Glu Cys
            245                 250                 255

Leu Ile Gly Asn Thr Thr Val Lys Val His Ala Ser Asp Glu Arg Leu
            260                 265                 270

Gly Pro Met Pro Cys Arg Pro Lys Glu Ile Val Ser Ser Ala Gly Pro
            275                 280                 285

Val Arg Lys Thr Ser Cys Thr Phe Asn Tyr Ala Lys Thr Leu Lys Asn
            290                 295                 300

Lys Tyr Tyr Glu Pro Arg Asp Ser Tyr Phe Gln Gln Tyr Met Leu Lys
305                 310                 315                 320

Gly Glu Tyr Gln Tyr Trp Phe Asp Leu Asp Val Thr Asp Arg His Ser
                325                 330                 335

Asp Tyr Phe Ala Glu
            340
```

<210> SEQ ID NO 19
<211> LENGTH: 429
<212> TYPE: DNA
<213> ORGANISM: Artificial Sequence
<220> FEATURE:
<223> OTHER INFORMATION: DNA sequence of cellulose binding domain

<400> SEQUENCE: 19
tttcgaagtt caccagtgcc tgcacctggt gataacacaa gagacgcata ttctatcatt    60
caggccgagg attatgacag cagttatggt cccaaccttc aaatctttag cttaccaggt   120

```
ggtggcagcg ccattggcta tattgaaaat ggttattcca ctacctataa aaatattgat    180
tttggtgacg gcgcaacgtc cgtaacagca agagtagcta cccagaatgc tactaccatt    240
caggtaagat tgggaagtcc atcgggtaca ttacttggaa caatttacgt ggggtccaca    300
ggaagctttg atacttatag ggatgtatcc gctaccatta gtaatactgc gggtgtaaaa    360
gatattgttc ttgtattctc aggtcctgtt aatgttgact ggtttgtatt ctcaaaatca    420
ggaacttct                                                           429

<210> SEQ ID NO 20
<211> LENGTH: 4
<212> TYPE: PRT
<213> ORGANISM: Artificial Sequence
<220> FEATURE:
<223> OTHER INFORMATION: Amino acid sequence of HDEL

<400> SEQUENCE: 20

His Asp Glu Leu
1
```